(12) United States Patent
Bagwell et al.

(10) Patent No.: US 10,387,617 B2
(45) Date of Patent: Aug. 20, 2019

(54) OPTIMIZATION OF MEDICINES DELIVERY

(71) Applicant: INTERNATIONAL BUSINESS MACHINES CORPORATION, Armonk, NY (US)

(72) Inventors: Derek P. Bagwell, Rochester, MN (US); Swaminathan Balasubramanian, Troy, MI (US); Mamnoon Jamil, Voorhees, NJ (US); Cheranellore Vasudevan, Bastrop, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/249,766

(22) Filed: Aug. 29, 2016

(65) Prior Publication Data

US 2018/0060517 A1   Mar. 1, 2018

(51) Int. Cl.
*G06F 19/00* (2018.01)
*A61J 7/04* (2006.01)

(52) U.S. Cl.
CPC ...... *G06F 19/3418* (2013.01); *G06F 19/3462* (2013.01); *A61J 7/04* (2013.01)

(58) Field of Classification Search
CPC ...... G06F 19/3418; G06F 19/3462; A61J 7/04
USPC ................................................. 700/231–244
See application file for complete search history.

(56) References Cited

U.S. PATENT DOCUMENTS

| | | | | |
|---|---|---|---|---|
| 6,421,650 B1* | 7/2002 | Goetz | ............... | G06F 15/025 128/205.23 |
| 6,909,359 B1* | 6/2005 | McGovern | ............ | A61J 7/0481 340/286.02 |
| 6,961,285 B2* | 11/2005 | Niemiec | ............... | A61B 5/0002 206/531 |
| 7,107,122 B1* | 9/2006 | Whyte | ............... | A61J 7/0481 221/12 |
| 7,698,157 B2* | 4/2010 | Ghouri | ............... | G06F 19/326 600/300 |
| 7,801,745 B2* | 9/2010 | Walker | ............... | G06F 19/3462 705/2 |
| 7,801,845 B1* | 9/2010 | King | ............... | G06Q 30/018 707/608 |
| 7,921,020 B2* | 4/2011 | Kalies | ............... | G06Q 50/22 705/2 |
| 8,483,872 B2 | 7/2013 | Ratnakar | | |
| 8,600,548 B2* | 12/2013 | Bossi | ............... | G06F 19/3462 700/240 |
| 9,659,037 B2* | 5/2017 | Soni | ............... | G06F 19/3418 |
| 2005/0149361 A1* | 7/2005 | Saus | ............... | G06F 19/326 705/3 |
| 2005/0240305 A1* | 10/2005 | Bogash | ............... | G06F 19/3462 700/242 |

(Continued)

*Primary Examiner* — Michael Collins
(74) *Attorney, Agent, or Firm* — Griffiths & Seaton PLLC (57) ABSTRACT

Embodiments for scheduling the delivery of multiple medications to a patient by a processor. Any interactions between the multiple medications or between one of the multiple medications and a type of food are considered to construct an analytical model to identify an optimized schedule for delivery of the multiple medications to the patient. The optimized schedule is adjusted in real time as additional information concerning the multiple medications and the type of food are introduced, and delivered to a dispensing device associated with the one of the multiple medications.

21 Claims, 7 Drawing Sheets

(56) References Cited

U.S. PATENT DOCUMENTS

| | | | | |
|---|---|---|---|---|
| 2005/0240444 A1* | 10/2005 | Wooten | ............... | G06F 19/3481 |
| | | | | 705/3 |
| 2006/0196928 A1 | 9/2006 | Castagna | | |
| 2007/0185615 A1* | 8/2007 | Bossi | ................. | G06F 19/3462 |
| | | | | 700/244 |
| 2008/0195249 A1* | 8/2008 | Rousso | ................. | A61B 5/417 |
| | | | | 700/231 |
| 2008/0235059 A1* | 9/2008 | Gonzalvo | ............ | G06F 19/3456 |
| | | | | 705/3 |
| 2009/0127275 A1* | 5/2009 | Choi | ..................... | A61J 7/0481 |
| | | | | 221/1 |
| 2009/0281835 A1 | 11/2009 | Patwardhan et al. | | |
| 2010/0096399 A1* | 4/2010 | Ratnakar | ................. | A61J 7/02 |
| | | | | 221/1 |
| 2010/0212675 A1* | 8/2010 | Walling | .............. | G06F 19/3418 |
| | | | | 128/898 |
| 2010/0218132 A1* | 8/2010 | Soni | ................... | G06F 19/3418 |
| | | | | 715/771 |
| 2014/0114472 A1* | 4/2014 | Bossi | ................. | G06F 19/3462 |
| | | | | 700/240 |
| 2014/0172160 A1* | 6/2014 | Patel | ................... | G06F 19/3462 |
| | | | | 700/233 |
| 2014/0236352 A1* | 8/2014 | Johnson | ................. | G04G 11/00 |
| | | | | 700/244 |
| 2014/0324800 A1* | 10/2014 | Soni | ................... | G06F 19/3418 |
| | | | | 707/694 |

* cited by examiner

OPTIMIZATION OF MEDICINES DELIVERY

BACKGROUND OF THE INVENTION

Field of the Invention

The present invention relates in general to computing systems, and more particularly to, various embodiments for providing an optimized medicine delivery schedule to patient by a processor.

Description of the Related Art

In today's society, various medical advances, coupled with advances in technology have made possible a wide variety of attendant benefits, such as the computerized monitoring of a patient, or the storing or organization of data representative of a patient's health records. As computers, processors, storage devices and mobile computing platforms proliferate throughout aspects of society, additional opportunities continue to present themselves for leveraging technology in health care for the benefit of patients, health professionals, and others.

SUMMARY OF THE INVENTION

Various embodiments for scheduling the delivery of multiple medications to a patient by a processor, are provided. In one embodiment, by way of example only, a method for scheduling the delivery of multiple medications to a patient, again by a processor, is provided. Any interactions between the multiple medications or between one of the multiple medications and a type of food are considered to construct an analytical model to identify an optimized schedule for delivery of the multiple medications to the patient. The optimized schedule is adjusted in real time as additional information concerning the multiple medications and the type of food are introduced, and delivered to a dispensing device associated with the one of the multiple medications.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Drug interactions may render a patient's drug less effective, cause unexpected side effects, or increase the action of a particular drug in the combination. Some drug interactions may even be harmful to the patient. Reading the label every time the patient uses a non-prescription or prescription medicine, and taking the time to learn about drug interactions may be critical to ensure the medicines work effectively, or do not cause any health detriments.

Drug interactions fall into three broad categories. First, drug-drug interactions occur when two or more drugs react with each other. This drug-drug interaction may cause unexpected side effects. Second, drug-food/beverage interactions may result from drugs reacting with certain foods or beverages. Finally, drug-condition interactions may occur when an existing medical condition makes certain drugs potentially harmful. For example, if the patient has high blood pressure, use of a particular nasal decongestant may lead to unexpected reactions.

If a patient is required to take multiple medicines, the schedule should take into consideration of staggering the administration time to avoid any possible interaction or nullifying actions. There are no tools available today to schedule the multiple drugs considering potential interactions between drugs and food. The problem becomes more complex when multiple physicians prescribe medicines that matter to their corresponding specialty. Also, in the future, "internet dispensed medicines" may become more popular where a human pharmacist, nurse, or physician may not be present to provide the advice on taking particular medicines.

While there are tools available to determine the dosage of drugs based on age and other patient conditions, determining the daily/other periodic schedules is often a major challenge. The mechanisms of the illustrated embodiments provide solutions for the determination and delivery of appropriate, optimized schedules for multiple medications to a patient, and involve health professionals, such as pharmacists, physicians across various disciplines, and other persons that may have an interest in the patient in the process, as will be further described. In addition, the advent of various interne connected devices in the so-called "Internet of Things" (IoT) discipline offers new avenues for addressing these challenges in a novel way, again as will be described.

In view of the foregoing, the mechanisms of the illustrated embodiments provide novel approaches to identify potential conflicting medications and create a corresponding schedule of multiple medicinal administration considering drug to drug and drug-food interactions. Among other aspects, the mechanisms of the illustrated embodiments introduce an IoT-centric analytical approach for the detection of potential interactions with multiple drugs, an analytical model that identifies an optimal schedule (if available) for administering multiple medications for a patient, a representation of the various reactions/dependent effects of differing medications, for example at the biochemical level, and types of food, and modeling of the rules governing drug-drug and drug-food interactions, which may be updated in real time based on new information introduced into the system as will be further described.

In an additional embodiment, the mechanisms of the present invention may collect patient or healthcare professional comments/feedback about personal experiences with multiple medications to determine the sentiment (positive or negative) of the experiences. Prior to a new patient being given the same medicine combination, the present invention may query these experiences to develop a set of rule-based methodologies for delivery of the multiple medications to the patient with the least negative side effects, for example, or other negative effects.

In addition, when a health professional validates certain feedback, the mechanisms of the illustrated embodiments may utilize the sentiment information to either raise or lower the dosage, delivery schedule, or other aspects so as to lower the patient's side effects. For instance, if the mechanisms observe from reported sensor data that certain combinations of medicines cause observed side effects, the rule-based methodology for medicine deliveries may be updated to reinforce a warning for that particular combination to the patient and/or health professional. In this manner the system continuously, and in real-time, updates these rule based underpinnings of the delivery methodology for certain medicine combinations. Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
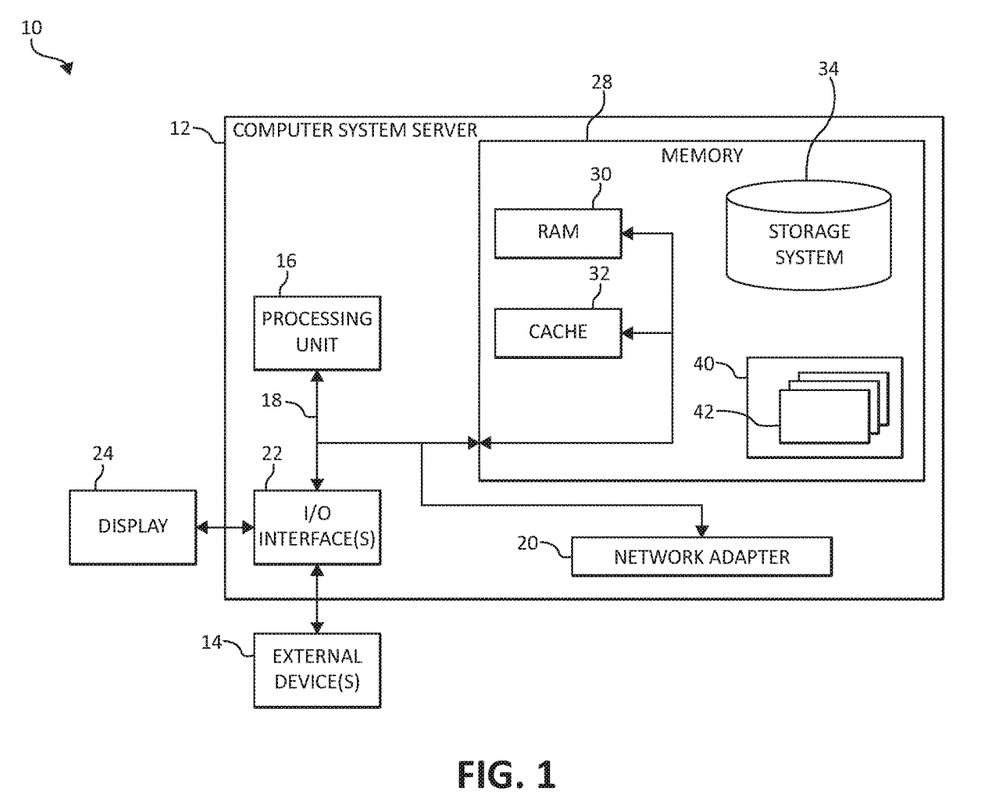
FIG. 1 is a block diagram depicting an exemplary cloud computing node according to an embodiment of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
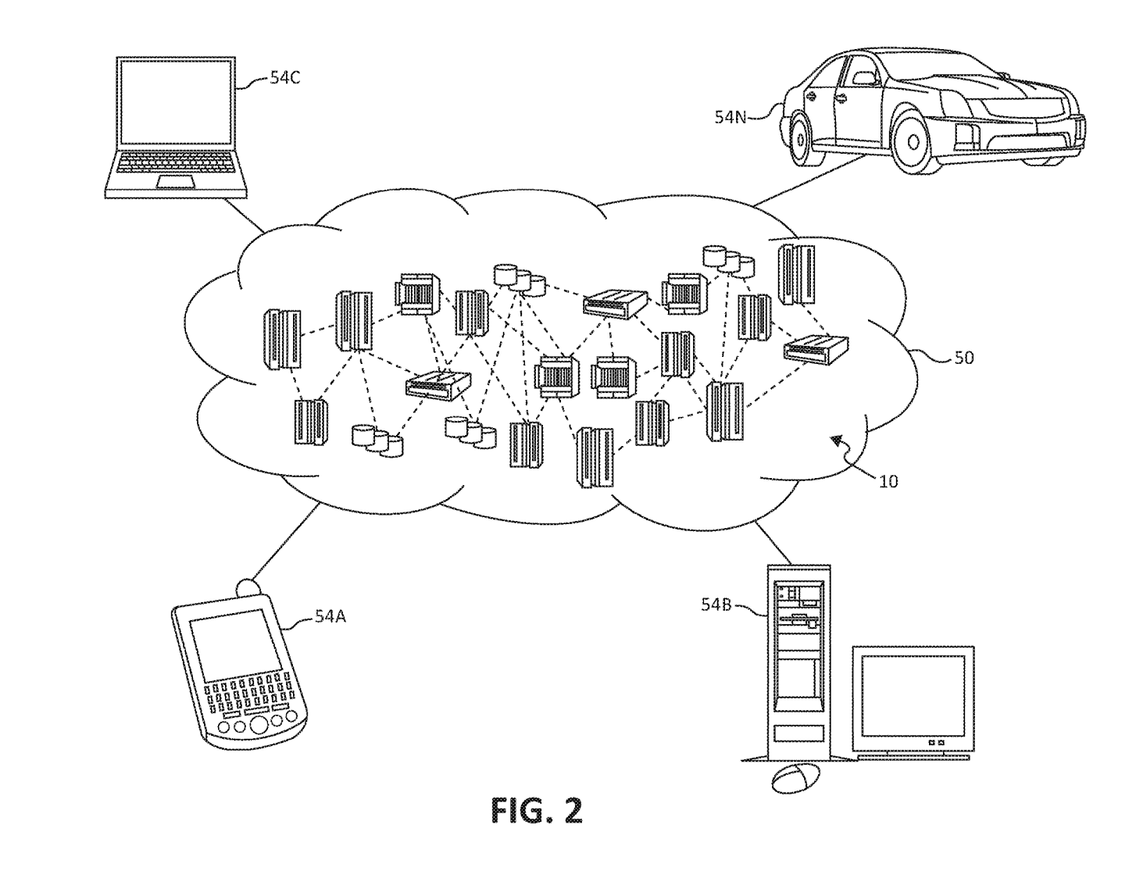
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
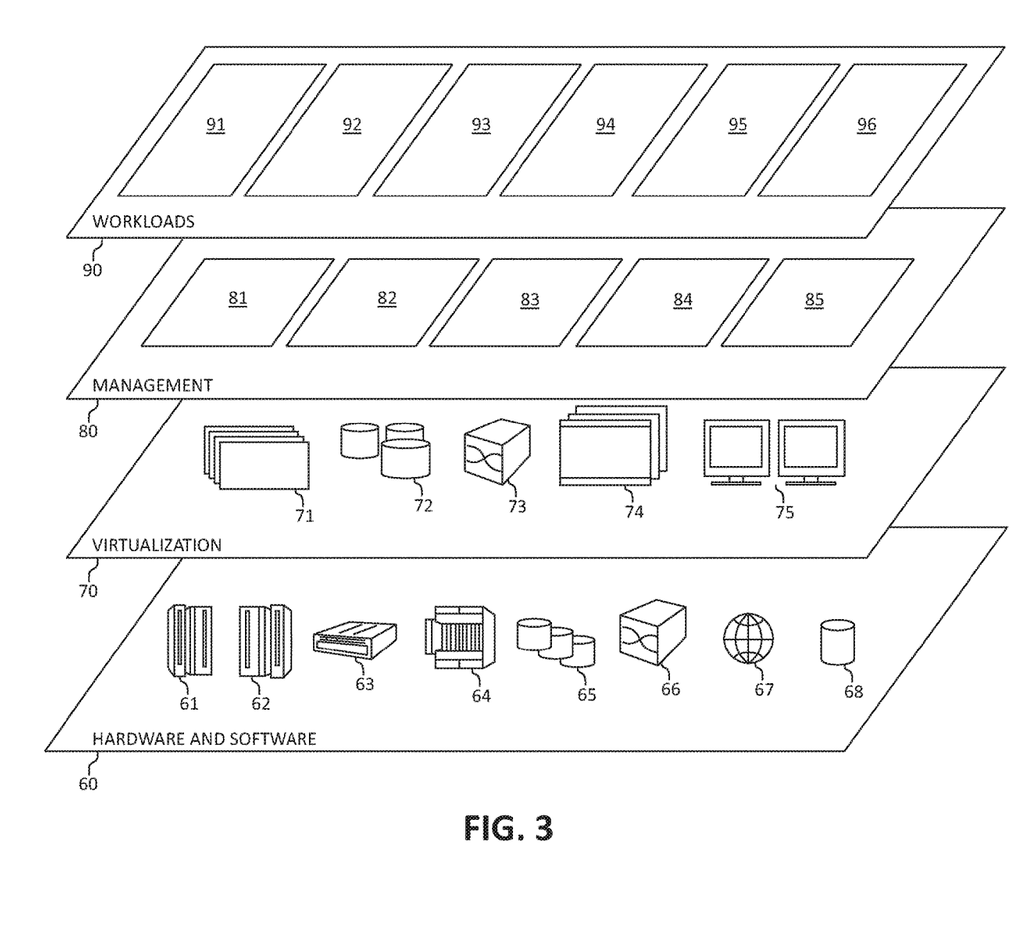
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various medicinal workloads and functions 96. In addition, communication processing workloads and functions 96 may include such operations as data analytics, data analysis, and as will be further described, scheduling functionality. One of ordinary skill in the art will appreciate that the medicinal workloads and functions 96 may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

Certain medications need to be taken together, and certain combinations may not be as effective, or even harmful. As previously mentioned, the mechanisms of the illustrated embodiments provide novel approaches for the real-time analysis of a patient's treatment regime of multiple medications, the construction of an optimized delivery schedule in view of these multiple medications (taking into account the various other medicines being currently taken by the patient as well as food or other environmental interactions such as time of year, age of the patient, gender, the patient's current health status, and a variety of other possible factors), and the delivery of the optimized delivery schedule to what will be termed herein as a "dispensing device" or "dispensary device" as will be further described.

In one embodiment, the dispensing device may be a so-called "smart medicine container." Such a smart medicine container may contain the medicines to be dispensing, incorporate lockable functionality or other security measures, for example, and connect to the Internet so as to send and/or receive information. The smart medicine container may perform such functionality as drug administration reminders, remote medicine management, disease management, and health education. In addition to the foregoing functionality, the mechanisms of the illustrated embodiments, as will be described, provide an optimized delivery schedule to the patient on each of the patient's smart containers. With multiple Internet-connected smart containers that may communicate (to a cloud-based decision engine, for example) details of the particular medicine contained, potential conflicts between all of the patient's medicines in their medicine cabinet (regardless of whether the patient is taking the medicine currently) may be thoroughly analyzed. In this manner, a comprehensive schedule may then be developed that is provided to each smart container for appropriate alerts/reminders/other communications as warranted and as personalized for each specific medicine contained.

In one embodiment, for example the data collected through multiple drug containers is used to check, validate, and generate the right medicine administration schedule based on the condition of the patient as well as specific ingredients of the particular medicine.

Figure 4:
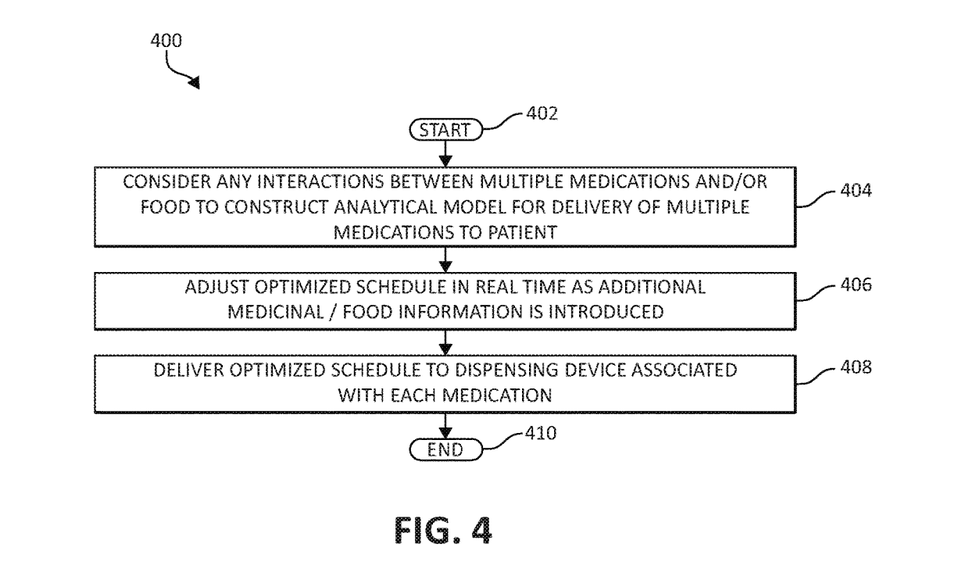
FIG. 4 is a flowchart diagram depicting an exemplary method for scheduling the delivery of multiple medications to a patient, in which various aspects of the present invention may be realized.

Turning now to FIG. 4, a flowchart of an exemplary method 400 for optimizing delivery of multiple medications to a patient by a processor is depicted, in which various aspects of the illustrated embodiments may be implemented. Method 400 begins (step 402) with the consideration of any interactions between multiple medications, food, and/or other environmental factors to construct an appropriate analytical model for delivery of an optimized administration schedule to the patient (step 404). As will be further described, the various aspects of step 404, along with other functional aspects of the method 400 will be further illustrated in detail, following in various embodiments.

Once the analytical model is developed, the constructed optimized schedule is then updated in real-time as additional medicinal, food, or other information is introduced (step 406). The optimized schedule is then delivered to a dispensing device associated with each of the multiple medications of the patient (step 408). As previously described, this schedule may be optimized for each particular medication in the patient's medicine cabinet, regardless of whether the patient is currently taking the medication. For example, the patient may occasionally take an over counter anti-inflammatory medicine for occasional arthritis pain. The mechanisms of the illustrated embodiments may optimize an administration of the over counter medication in view of each of the additional medications that the patient is currently taking, so that if the patient does have a flare up, the patient can retrieve the pertinent dispensing information from the dispensing device associated with the anti-inflammatory medication (e.g., such as a smart container). The method 400 then ends (step 410).

Figure 5:
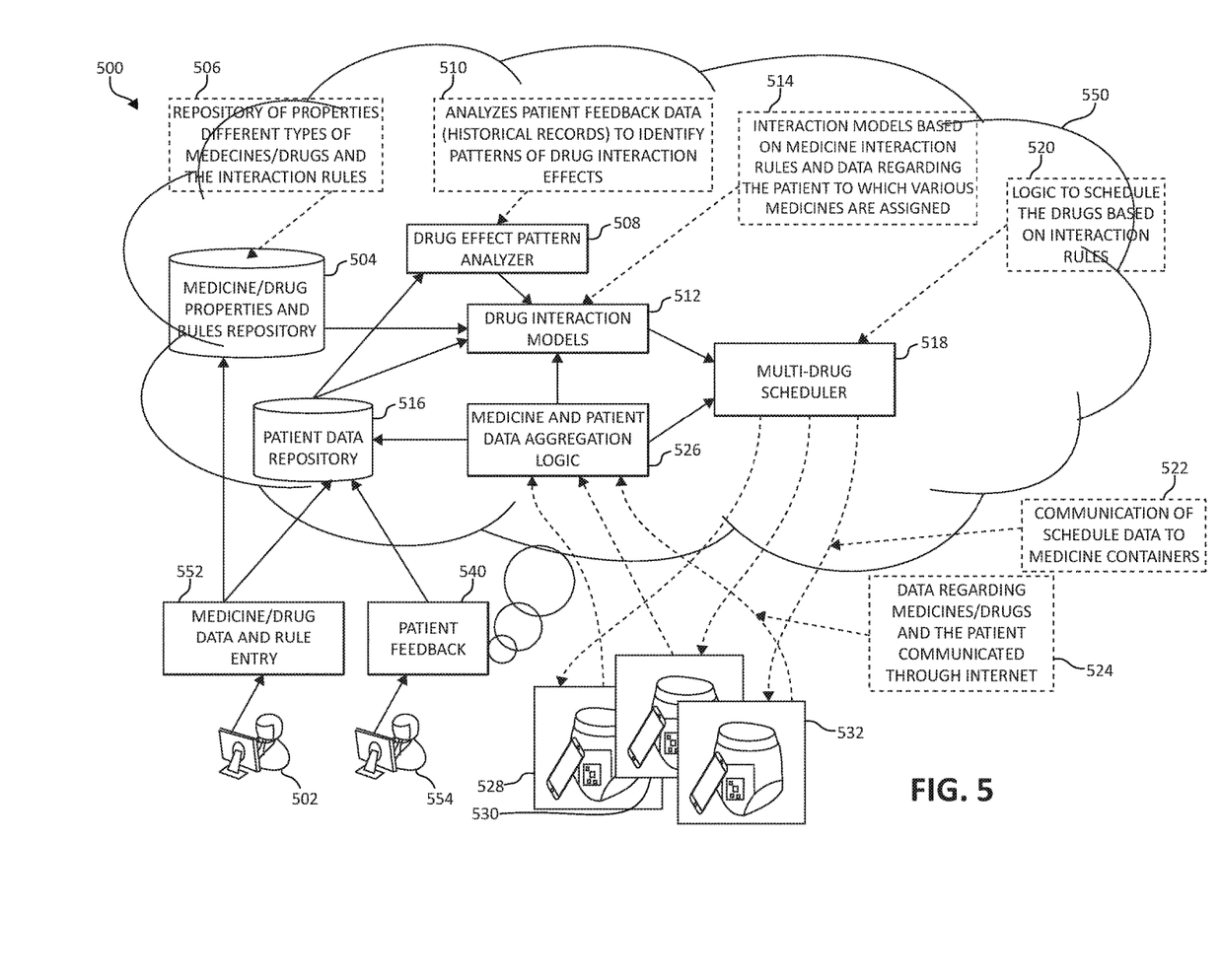
FIG. 5 is a block/flow diagram illustrating certain aspects of functionality according to the present invention.

In view of the method 400 of FIG. 4, consider, as an illustration of exemplary functional blocks to accomplish various purposes of the present invention, FIG. 5, following. FIG. 5 illustrates these exemplary functional blocks 500 and associated notes on specific functionality (as denoted by the doted boxes). Each of the functional blocks 500 may be implemented in hardware and/or software, such as by the computer/server 12 (FIG. 1), and/or the workloads layer 90 (FIG. 3), or other implementations known to one of ordinary skill in the art.

In the depicted embodiment, a patient, medical professional (such as a physician, pharmacist, nurse, and so forth), or other interested person 502 makes data entries 552 pertaining to particular medicine information and with the medicine information, certain rules. The rules may be constructed by the individual and/or by the system interpreting the various medical information submitted. The data entries may include such information as typical dosage strengths, known contraindications, allergy information, food interactions, and various other kinds of information. Each of the data entries and interpreted and/or entered rules is then stored in a medicine/drug properties and rules repository 504, such as a database, and as indicated by dotted box of functionality 506. The repository 504 provides a storage location of various medicinal properties, various kinds of medicines/drugs, and various interactions. In addition, the repository 504 includes the interpreted and/or entered rules from the data entries.

In addition, and as shown, the patient, medical professional or other person 554 may also provide feedback information 540 that is supplied to a patient data repository 516. The patient or other professional feedback's role in the mechanisms of the illustrated embodiments will be further described below, but as an initial matter, the feedback may be implemented as a learning mechanism by the functional blocks 500 to adjust various rules for medication delivery, or validate current delivery regimes, for example.

Data from the medicine/drug data and rule entry process also makes way to a patient data repository 516, where the information may be combined with various patient information, such as age, gender, sensitivities, allergies, and other relevant patient information for the system to make various inferences between each of the prescribed medications, food intake, and other factors to calculate an optimized administration schedule. As shown, information from the patient data repository 516 is provided to the drug effect pattern analyzer 508, which, among other aspects, analyzes patient feedback data (e.g., historical records) to identify patterns of drug interaction effects (as shown by dotted functionality box 510).

Information from the medicine/drug data 552/504, patient information and feedback (and related information) 540/516, and processed information from the drug effect pattern analyzer 508 is considered, analyzed, weighted, and used to calculate various drug interaction models in functional block 512. In one embodiment, the interaction models 512 are based on medicine interaction rules and data regarding the patient to which the various medicines are assigned (e.g., prescribed and/or taking), as indicated by dotted functionality box 514.

Data from the drug interaction models 512, as well as various medicine and patient data aggregation logic 526 is provided to the multidrug scheduler function 518. The multidrug scheduler 518, among other aspects, incorporates logic to schedule delivery of the medicines based on the various interaction rules, as indicated by dotted functionality box 520. The resulting functionality obtained from the multidrug scheduler 518, coupled with the medicine and patient data aggregation logic 526, affords bidirectional communication between the blocks of functionality 500 and various dispensing devices 528, 530, and 532. For example, the functional blocks 500 convey communication of scheduling data to the dispensing devices, as indicated by dotted functionality box 522. Among other aspects, data regarding medicines/drugs and the subject patient may be communicated over various communications networks (local networks, wired and wireless networks, and any other communications paths known to one of ordinary skill in the art), including portions of the Internet as indicated by the dotted functionality box 524.

One aspect of the mechanisms of the illustrated embodiments includes the implementation of collection of interconnected dispensing devices, such as "smart Internet-enabled medicine containers." These containers may transmit information about the medicine and associated types and dosage prescribed along with patient identification information. In one embodiment, this information from one or more medicine containers may be received and aggregated by a cloud-based system having two repositories; a patient data repository and medicine properties and rule repository. The rules coupled with medicine properties information are used along with the specific combination of medicines of a patient to build a patient-specific drug-interaction model. This model is used to validate/check for conflicts. Moreover, if possible, the generated schedule is computed based on the most effective usage of the medicines. This information is transmitted back to the appropriate medicine containers so that these smart devices may advise/alert/remind patients for appropriate dispensing.

Figure 6:
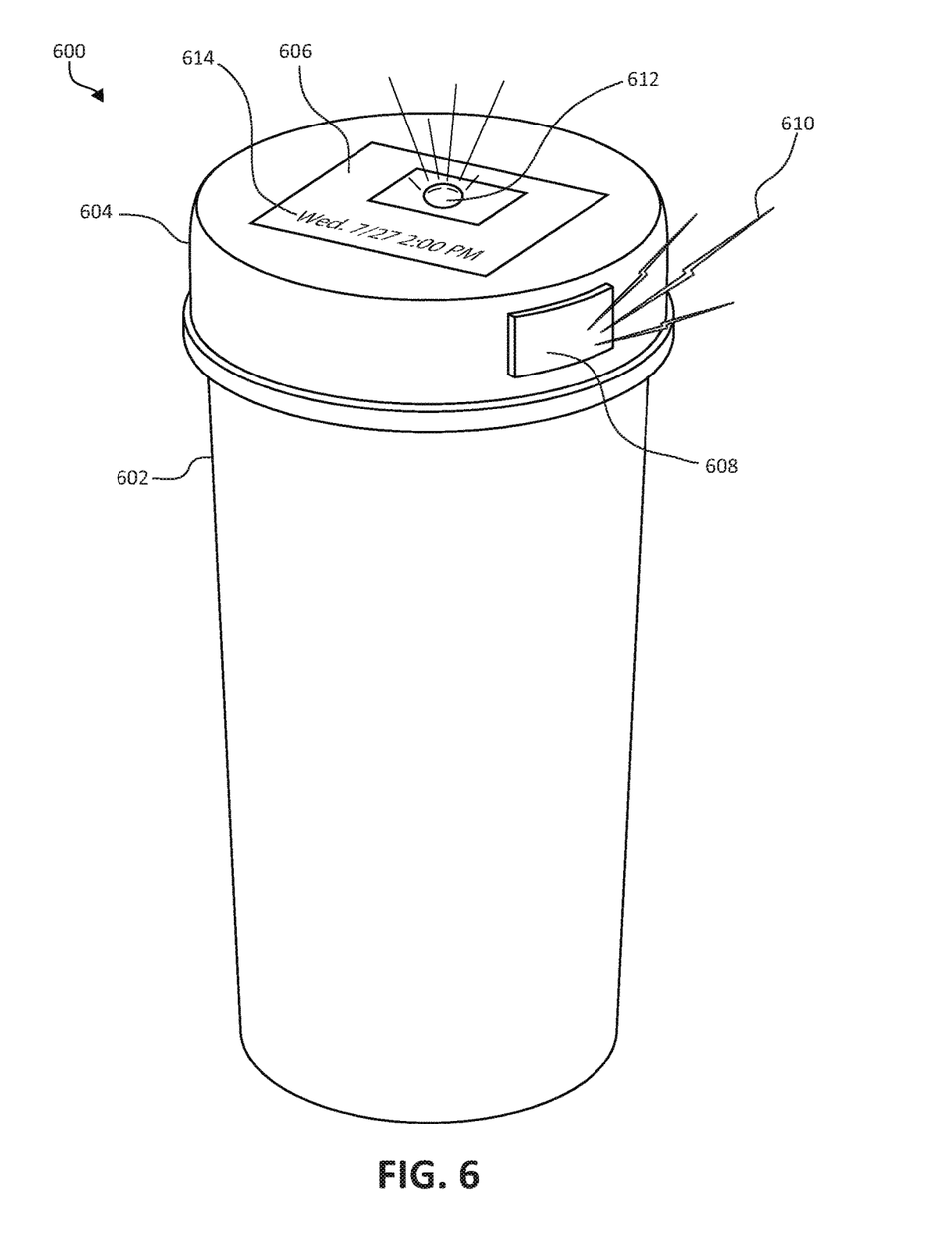
FIG. 6 is a block diagram illustrating an exemplary dispensing device, again in which various aspects of the present invention may be realized.

FIG. 6, following, illustrates an exemplary dispensing device 600 that may be afforded various aspects of the present invention. The dispensing device may be considered a smart medicine container 602 or a smart pharmacy bottle 602, for example and as previously described. The smart medicine container 602 includes a lid structure 604, a display structure 606 such as a liquid crystal display (LCD), light emitting diode (LED) display structure or another inexpensively manufactured display structure known to one of ordinary skill in the art.

In addition, the smart medicine container 602 incorporates an audio generating structure 608, such as a miniaturized loudspeaker 608, or a similar device 608 that generates an auditory cue to the patient. The smart medicine container may use any number of wireless communications protocols 610 such as 802.11 Wi-Fi communications, Bluetooth® communications protocols, and any other wireless communications protocols known to one of ordinary skill in the art.

A portion 612 of the display 606 is shown to be blinking to indicate that the next appropriate delivery date/time for dispensing the medication to the patient has arrived, as shown by display alert 614. Here, Wednesday, July 27, at 2:00 PM has been determined by the system to be the next appropriate/optimized time for delivery of this particular medication (in the context of the patient's other medications) to the patient. Accordingly, the smart medicine container 602 has provided a visual cue as display alert 614 (and/or possibly an auditory cue from the audio generating structure 608) to the patient to indicate that the designated time has arrived.

Figure 7:
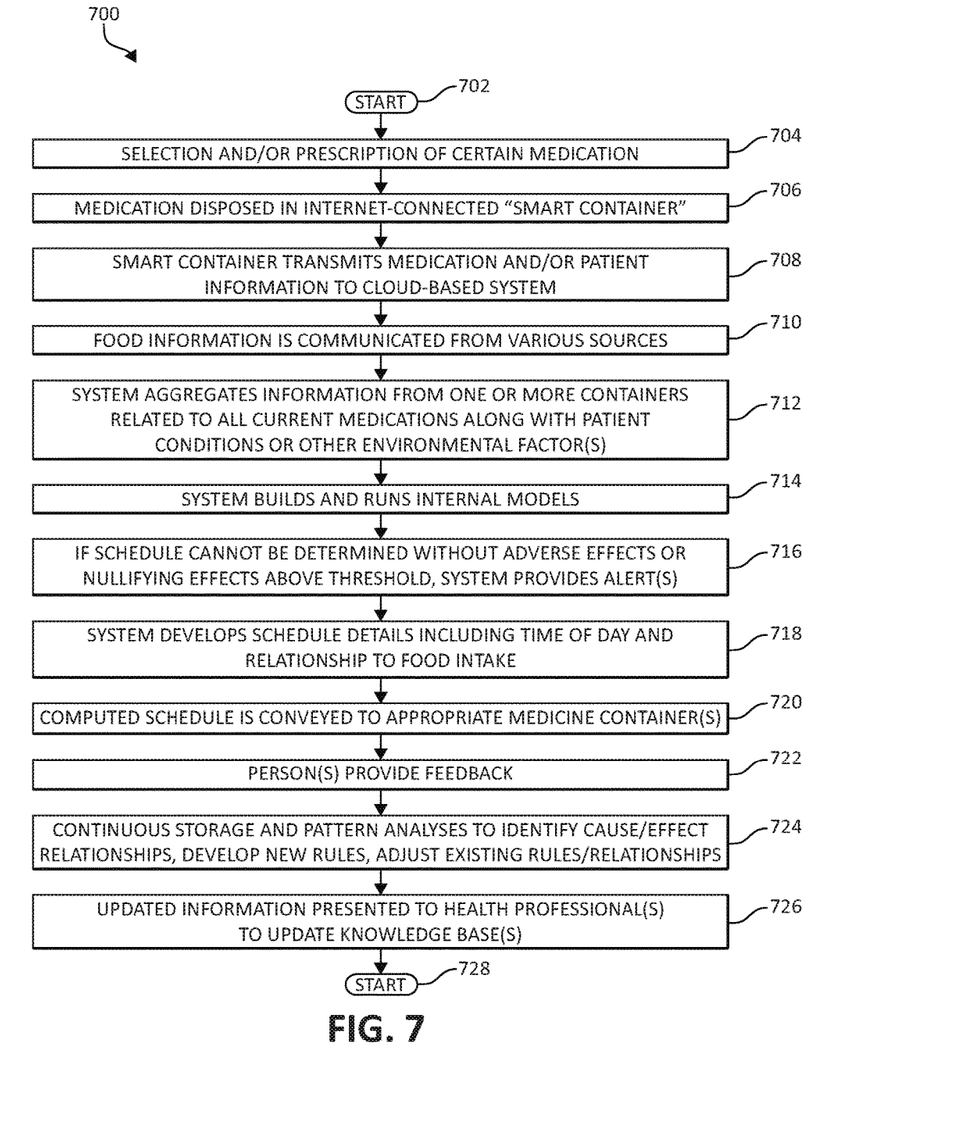
FIG. 7 is an additional flowchart diagram depicting an additional exemplary method for scheduling the delivery of multiple medications to a patient, again in which various aspects of the present invention may be realized.

Turning now to FIG. 7, an additional flowchart of an exemplary method 700 for facilitating an optimized multiple-medicine delivery schedule to a patient is depicted, here again in which various aspects of the present invention may be realized. Method 700 begins (step 702), with the prescription (by a physician) or selection of an over-the-counter type (by the patient) of a particular medicine in step 704. The particular medicines are disposed in pre-configured delivery devices, such as Internet-connected smart containers (step 706). The smart containers transmit medicinal and patient information to a cloud-based system (step 708).

In a subsequent step 710, various information concerning the type(s) of food being ingested by the patient is collected. This information may be supplied by the health professional, the user, by administrators, or others. The system then aggregates the information from one or more (e.g., all containers in the medicine cabinet of the patient) containers, along with patient conditions (age, other significant health status, environmental factors), or a possible wide variety of other information that may be relevant to the patient's current health condition (step 712). The system then builds and executes the relevant internal model using the various medicine compositions and corresponding data to appropriately stagger the quantity, for example, and/or time of intake, for example, that would avoid any potentially harmful reactions (step 714).

If the administration of the various medicines cannot be scheduled without adverse effects or nullifying effects, the system generates an appropriate message(s) to indicate which medicines cannot be scheduled, including stating the relevant reasons for the inability to schedule (step 716). The finalized, optimized schedule may include the time of day, before/after food, time elapse (if staggered), time between food intake, and a wide variety of potential other administration information (step 718). The computed schedule is then conveyed as tailored to each of the specific dispensing devices, such that each of the devises may dispense, provide alerts, and reminders as appropriate, and specific to the medicine contained within or associated with each dispensing device (step 720).

In a subsequent step 722, the patient (based on their experiences/symptoms with an existing delivery regime), healthcare professional, or other person provides feedback into the system. The feedback undergoes continuous storage and pattern analyses to generate new rules/modifications to existing rules, for example (step 724). Any newly discovered cause/effect relationships that may be considered "new rules" may then be presented to health care professionals (such as an attending physician, pharmacist, or pharmacologist) to update relevant knowledge bases and assist other professionals in treatment (step 726). The method 700 then ends (step 728).

It should be noted, additionally, that when an existing, specific medicine is withdrawn from a patient's regimen, or newly prescribed by a physician or selected over-the-counter by the patient, the previous steps 702-728 may then be re-executed as needed so as to accurately represent an effective delivery schedule for the totality of the medications taken by the patient. As the new medication is introduced, food information is introduced, medications are withdrawn, a new environmental factor is introduced (e.g., patient manifests an allergy to a specific ingredient), or any other information becomes available that is relevant to the optimized schedule, the optimized schedule may then be recomputed in real-time to accommodate. Any changes to times, dosages, or other administration information may then be re-broadcast to each of the smart medicine containers to reflect the appropriate updates.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for scheduling the delivery of multiple medications to a patient by a processor, comprising:
considering any interactions between the multiple medications or between one of the multiple medications and a type of food to construct an analytical model to identify an optimized schedule for delivery of the multiple medications to the patient regardless of whether the patient is currently taking the multiple medications such that those of the multiple medications not explicitly prescribed to the patient notwithstanding the patient desires to take occasionally, when taken and input to the analytical model, will update the optimized schedule for delivery at a time when those of the multiple medications are taken; wherein the optimized schedule is:
automatically adjusted, by the processor, in real time as additional information concerning the multiple medications and the type of food are introduced such that a recent food intake of the patient is used to adjust the optimized schedule in real time according to any considered interactions, and
delivered to a dispensing device associated with the one of the multiple medications, the dispensing device comprising a portable smart medicine container having a liquid crystal display (LCD) or light emitting diode (LED) display for displaying the optimized schedule to the patient.

2. The method of claim 1, further including initializing a tool connected as an Internet of Things (IoT) appliance to present the optimized schedule to the patient.

3. The method of claim 1, further including building a representation of the interactions between the multiple medications or food to be delivered in addition to the optimized schedule to the patient.

4. The method of claim 1, further including:
receiving data representative of the one of the multiple medications or the patient from the dispensing device, or
transmitting at least a portion of the optimized schedule for delivery of the multiple medications to the dispensing device.

5. The method of claim 1, further including notifying the user of at least a portion of the optimized schedule for delivery of the multiple medications via the dispensing device using a visual or auditory cue.

6. The method of claim 1, further including analyzing feedback from the patient regarding the interactions between the multiple medications or between the one of the multiple medications and the type of food to develop a rule used in developing the optimized schedule for delivery of the multiple medications to the patient or an additional patient.

7. The method of claim 6, further including delivering the feedback or the developed rule to a health professional.

8. A system for scheduling the delivery of multiple medications to a patient, comprising:
a processor, operational within and between a distributed computing environment, that considers any interactions between the multiple medications or between the one of the multiple medications and a type of food to construct an analytical model to identify an optimized schedule for delivery of the multiple medications to the patient regardless of whether the patient is currently taking the multiple medications such that those of the multiple medications not explicitly prescribed to the patient notwithstanding the patient desires to take occasionally, when taken and input to the analytical model, will update the optimized schedule for delivery at a time when those of the multiple medications are taken, wherein the optimized schedule is:
automatically adjusted, by the processor, in real time as additional information concerning the multiple medications and the type of food are introduced such that a recent food intake of the patient is used to adjust the optimized schedule in real time according to any considered interactions, and
delivered to a dispensing device associated with the one of the multiple medications, the dispensing device comprising a portable smart medicine container having a liquid crystal display (LCD) or light emitting diode (LED) display for displaying the optimized schedule to the patient.

9. The system of claim 8, wherein the processor initializes a tool connected as an Internet of Things (IoT) appliance to present the optimized schedule to the patient.

10. The system of claim 8, wherein the processor builds a representation of the interactions between the multiple medications or food to be delivered in addition to the optimized schedule to the patient.

11. The system of claim 8, wherein the processor:
receives data representative of the one of the multiple medications or the patient from the dispensing device, or
transmits at least a portion of the optimized schedule for delivery of the multiple medications to the dispensing device.

12. The system of claim 8, wherein the processor notifies the user of at least a portion of the optimized schedule for delivery of the multiple medications via the dispensing device using a visual or auditory cue.

13. The system of claim 8, wherein the processor analyzes feedback from the patient regarding the interactions between the multiple medications or between the one of the multiple medications and the type of food to develop a rule used in developing the optimized schedule for delivery of the multiple medications to the patient or an additional patient.

14. The system of claim 13, wherein the processor delivers the feedback or the developed rule to a health professional.

15. A computer program product for scheduling the delivery of multiple medications to a patient by a processor, the computer program product comprising a non-transitory computer-readable storage medium having computer-readable program code portions stored therein, the computer-readable program code portions comprising:
an executable portion that considers any interactions between the multiple medications or between one of the multiple medications and a type of food to construct an analytical model to identify an optimized schedule for delivery of the multiple medications to the patient regardless of whether the patient is currently taking the multiple medications such that those of the multiple medications not explicitly prescribed to the patient notwithstanding the patient desires to take occasionally, when taken and input to the analytical model, will update the optimized schedule for delivery at a time when those of the multiple medications are taken, wherein the optimized schedule is:
automatically adjusted, by the processor, in real time as additional information concerning the multiple medications and the type of food are introduced such that a recent food intake of the patient is used to adjust the optimized schedule in real time according to any considered interactions, and
delivered to a dispensing device associated with the one of the multiple medications, the dispensing device comprising a portable smart medicine container having a liquid crystal display (LCD) or light emitting diode (LED) display for displaying the optimized schedule to the patient.

16. The computer program product of claim 15, further including an executable portion that initializes a tool connected as an Internet of Things (IoT) appliance to present the optimized schedule to the patient.

17. The computer program product of claim 15, further including an executable portion that builds a representation of the interactions between the multiple medications or food to be delivered in addition to the optimized schedule to the patient.

18. The computer program product of claim 15, further including an executable portion that:
receives data representative of the one of the multiple medications or the patient from the dispensing device, or
transmits at least a portion of the optimized schedule for delivery of the multiple medications to the dispensing device.

19. The computer program product of claim 15, further including an executable portion that notifies the user of at least a portion of the optimized schedule for delivery of the multiple medications via the dispensing device using a visual or auditory cue.

20. The computer program product of claim 15, further including an executable portion that analyzes feedback from the patient regarding the interactions between the multiple medications or between the one of the multiple medications and the type of food to develop a rule used in developing the optimized schedule for delivery of the multiple medications to the patient or an additional patient.

21. The computer program product of claim 15, further including an executable portion that delivers the feedback or the developed rule to a health professional.

* * * * *